(12) United States Patent
Weller

(10) Patent No.: US 8,450,081 B2
(45) Date of Patent: May 28, 2013

(54) IDENTIFICATION OF PATHOGENS IN BODY FLUIDS

(75) Inventor: Ulrich Weller, Cologne (DE)

(73) Assignee: Bruker Daltonik GmbH, Bremen (DE)

( * ) Notice: Subject to any disclaimer, the term of this patent is extended or adjusted under 35 U.S.C. 154(b) by 235 days.

(21) Appl. No.: 12/734,719

(22) PCT Filed: Nov. 20, 2008

(86) PCT No.: PCT/EP2008/009807
§ 371 (c)(1),
(2), (4) Date: May 19, 2010

(87) PCT Pub. No.: WO2009/065580
PCT Pub. Date: May 28, 2009

(65) Prior Publication Data
US 2010/0255527 A1 Oct. 7, 2010

(30) Foreign Application Priority Data

Nov. 23, 2007 (DE) .......................... 10 2007 056 583
Dec. 5, 2007 (DE) .......................... 10 2007 058 516

(51) Int. Cl.
*C12Q 1/02* (2006.01)
*C12N 11/02* (2006.01)

(52) U.S. Cl.
USPC ........................................... 435/29; 435/177

(58) Field of Classification Search
None
See application file for complete search history.

(56) References Cited

U.S. PATENT DOCUMENTS

| 4,350,767 | A | 9/1982 | Zimmermann | |
|---|---|---|---|---|
| 6,558,946 | B1 * | 5/2003 | Krishnamurthy | .......... 435/288.6 |
| 2002/0138210 | A1 | 9/2002 | Wilkes | |
| 2003/0022270 | A1 | 1/2003 | Seaver | |

FOREIGN PATENT DOCUMENTS

| DE | 197 07 508 | 8/1998 |
|---|---|---|
| DE | 100 38 694 | 2/2002 |
| DE | 103 00 743 | 7/2004 |
| DE | 10 2004 018 347 | 10/2005 |
| GB | 2 187 035 | 8/1987 |
| WO | WO 02/21108 | 3/2002 |

OTHER PUBLICATIONS

Edwards-Jones et al. Rapid Discrimination Between Methicillin-Sensitive and Methicillin-Resistant *Staphylococcus aureus* by Intact Cell Mass Spectromery; Journal of Medical Microbiology, vol. 49 (2000) pp. 295-300.*
Madonna et al. Detection of Bacteria From Biological Mixtures Using Immunomagnetic Separation Combined With Matrix-Assisted Laser Desorption/Ionization Time-of-Flight Mass Spectrometry; Rapid Communications in Mass Spectrometry, vol. 15 (2001) pp. 1068-1074.*
Maier et al. Rapid Identification of Bacteria From Blood Cultures Using MALDI-TOF MS; Meeting Poster, 48th Annual ICAAC/IDSA 46th Annual Meeting Washington, D.C. Oct. 25-28, 2008.*
Sawhney et al. Novel Method for Detecting Micro-Organisms in Blood Cultures; Journal of Clinical Pathology, vol. 39 (1986) pp. 1259-1263.*
Schwarz et al. Rapid Identification of Bacteria Causing Urinary Tract Infections by MALDI-TOF MS; Meeting Abstract, 48th Annual ICAAC/IDSA 46th Annual Meeting, Washington, D.C. Oct. 25-28, 2008.*
Letarte S. et al., "Py-MAB-Tof detection and Identification of microorganisms in urine", Journal of Analytical and Applied Pyrolysis Mar. 2004, Elsevier NL, vol. 71, No. 1, pp. 13-25.
Maier, T. et al., "Fast and reliable MALDI-TOF MS-based microorganism identification", Nature Methods 200604 GB, vol. 3, No. 4, Apr. 2006, Pa.i-ii.
Fenselau C. et al., "Characterization of intact microorganisms by MALDI mass spectrometry", Mass Spectrometry Reviews Jul.-Aug. 2001, vol. 20, No. 4, Jul. 2001, Pa. 157-171.
Evason D.J., et al., "Exploring the limits of bacterial identification by intact cell-mass spectrometry", Journal of the American Society for Mass Spectrometry, Elsevier Science Inc, US, vol. 12, No. 1, Jan. 2, 2001, Pa. 49-54.
"Managing Urinary Tract Infection in Women", Drug and Therapeutics Bulletin, Consumers Association, London, GB, vol. 36, No. 4, Apr. 1, 1998, Pa. 30-32.

* cited by examiner

*Primary Examiner* — Allison Ford
*Assistant Examiner* — Paul Martin
(74) *Attorney, Agent, or Firm* — Paul Vincent

(57) ABSTRACT

Identification of infectious pathogens, particularly viruses, bacteria and other microorganisms is effected with a method whereby pathogens of acute infections can be identified, without first culturing them in external nutrient media, by mass spectrometric measurement of their protein profiles obtained from pathogens directly precipitated from body fluid into pellets by centrifuging. With this method, pathogens which cause acute infections can be identified in less than one hour.

14 Claims, No Drawings

IDENTIFICATION OF PATHOGENS IN BODY FLUIDS

This application is the national stage of PCT/EP2008/009807 filed on Nov. 20, 2008 and also claims Paris Convention priority to DE 10 2007 056 584.8 filed on Nov. 23, 2007 and to DE 10 2007 058 516.2 filed on Dec. 5, 2007.

BACKGROUND OF THE INVENTION

The invention relates to the identification of infectious pathogens, particularly viruses, bacteria and other microorganisms.

The invention provides a method whereby pathogens of acute infections can be identified, without first culturing them in external nutrient media, by mass spectrometric measurement of their protein profiles obtained from pathogens directly precipitated from body fluid into pellets by centrifuging. With this method, pathogens which cause acute infections can be identified in less than one hour.

Many kinds of microorganism (which will also be referred to below as microbes), particularly bacteria and unicellular fungi, are very easy to identify by a recently introduced mass spectrometric process in which small quantities of microbes from a colony cultivated in the usual way in a nutrient medium are transferred to a mass spectrometric sample support plate, and then subjected directly to mass spectrometric analysis. The mass spectrum especially shows the different proteins, provided they are present in the microbes in sufficient concentration. The identity is then determined from the microbe's protein profile through reference to spectral libraries containing thousands of reference spectra.

The nutrient medium is usually contained in moist gelatine in a Petri dish, and separate colonies of pure strains are obtained from swabs in the usual way by culturing in about six to twenty hours, depending on the growth rate of the microbes. If the colonies overlap or become mixed, it is possible to obtain pure colonies, also in the usual way, by culturing a second time. A quantity of microbe culture is transferred with a small spatula, stick or pestle from a selected colony onto the mass spectrometric sample support plate and a solution of a conventional matrix substance for ionization by matrix assisted laser desorption (MALDI) is sprinkled on. The organic solvent in the matrix solution usually penetrates into the microbe cells and destroys them by osmotic force. The sample is then dried by evaporating the solvent, leading to crystallization of the dissolved matrix material. Soluble proteins and also, to a small extent, other cell substances become incorporated as analyte molecules into the matrix crystal.

The matrix crystals with the embedded analyte molecules are exposed to pulsed laser light in a mass spectrometer, which generates ions of the analyte molecules. The analyte ions can then be measured according to their mass in the mass spectrometer. Time-of-flight mass spectrometers are used preferably for this purpose. The mass spectrum is the profile of mass values and intensities of these analyte ions. Protein ions predominate; the most useful information is found in the mass range between about 3,000 and 15,000 daltons. In this method, practically all protein ions carry a single charge only (number of charges $z=1$), which means that it is possible here simply to speak of the mass m of the ions rather than always using the term "mass-to-charge ratio", m/z, as is otherwise usual—and necessary—in mass spectrometry.

This protein profile is highly characteristic of the particular microbe because every species of microbe produces its own, genetically programmed proteins, each with a characteristic mass. The protein profiles are characteristic for microbes in rather the same way as fingerprints are for people. Reliable libraries of mass spectra of the protein profiles of microbes, suitable for medical and legal applications (so called "validated libraries"), are nowadays being developed with cooperation from many sites, including diagnostics companies, university institutes, hospitals, and national institutes.

This identification method has proved to be extraordinarily successful. The certainty of correct identification is much greater than was possible with the microbiological identification methods used in the past. It has been demonstrated that the reliability of identification is well over 95 percent for hundreds of different kinds of microbes. However, it proved difficult to determine the reliability properly because the microbes from the known collections have been wrongly identified in more than only a few cases. In the end, only genetic sequencing can help to put the identification beyond any doubt and this has confirmed the mass spectrometric identification in the great majority of cases.

In many cases, this simple procedure even makes it possible to distinguish closely related strains of the same species of microbes, as the proteins present in microbes are genetically programmed and can vary distinctly between strains. Small changes in the genetic blueprint necessarily result in proteins with a different structure and masses that differ from genetically unmodified proteins; they therefore yield a different protein profile, provided the concentration of the proteins with changed mass in the microbes is sufficient to produce a signal strong enough for mass spectrometric analysis. It has already been possible to correct taxonomic classifications and relationships of microbes in this way.

If no reference mass spectrum is present in a library for the precise species of microbe being examined (which often happens, due to the hundreds of thousands of microbe species and the limited size of spectrum libraries so far available), library searches with looser similarity requirements can provide at least some indication of the order, family or genus of the microbes, since related microbes frequently contain a number of identical protein types.

For the protein ions of identical microbe species, the masses are, by their nature, always identical and therefore strictly reproducible, but the intensities of the protein signals reproduce only approximately. The use of different nutrient media for the culture has an effect on the metabolism of the microbes and therefore on the creation of the different proteins in varying proportions and so on their concentration and their intensity in the protein profile. The effect is, however, not strong. The variations in intensity do not interfere with the identification, provided a suitable computer program is used. Equally, the maturity of the colonies has an effect on the relative intensities of the protein signals in the mass spectra and here again only to a small extent. Characteristically different mass spectra from the same species of microbe are in fact only found in the case of microbes which can adopt different life-forms, such as spore-formers: the spores exhibit different protein profiles from the normal cells. If freshly cultured microbes are used, however, this difference is not important.

Computer programs for searching libraries and performing spectral comparisons can cope with variations in intensity, which only play a subsidiary role here. As has been noted above, the identification of microbes with these programs is very reliable. The programs operate without identifying the individual proteins involved (which could be done by means of fragment ion spectra), only using the similarity of the mass spectra. In the similarity search, masses are regarded as highly significant and intensities as much lower significant. It is even possible for some proteins to be absent from the mass spectra (due to very low intensity) without interfering with the similarity determination: matching the mass values for a large majority of proteins is enough for identification. Usually the library spectra store information as to which protein signals must always be present, for instance, by storing thresholds for the intensities, or information about the probability of finding the protein signals under observation in frequently repeated spectral recordings of different samples.

The reference spectra in the spectral libraries can, for instance, contain the masses, mass tolerances, mean intensities, standard deviations of the intensities, and appearance probabilities of the individual protein signals. The reference spectra are generally obtained from frequently performed raw measurements, preferably from different cultures, by automatic computer evaluation; they can also, however, be reduced by including additional knowledge about the microbes (see, for instance, the patent publications DE 100 38 694 A1 and DE 103 00 743 A1, W. Kallow et al.).

The method briefly described above, in which a few microbes from a colony are smeared onto a reserved spot on a mass spectrometric sample support, followed by sprinkling with matrix solution, is the simplest method of sample preparation and, so far, the fastest. The process can also be automated with the aid of image-recognizing pi-petting robots for use in routine laboratories. After culturing a colony that is only just visible, it only takes one or two hours to achieve full identification, even if hundreds of samples have to be analyzed at the same time. Mass spectrometric sample support plates for 96 or 384 samples are commercially available; it takes between about half an hour and two hours to record these mass spectra. For rush jobs, individual microbe samples can be identified within a few minutes, although culturing, which always takes time, is necessary first.

Other methods of sample preparation have also been investigated, such as extraction of the proteins after destroying the microbes ultrasonically in a tube, or extraction methods for the proteins after dissolving the sometimes resistive cell walls using strong acids. These methods of decomposition are used when the normal method of smearing the microbes fails due to the microbe cell walls not being destroyed when the matrix solution is sprinkled on. If the normal method yields enough good mass spectra for a comparison, the decomposition methods give results that are very similar to the simple smearing method, but do often exhibit clearer mass spectra with less background interference. Both methods yield mass spectra which can identify the microbes using the same library of reference mass spectra.

Today, the mass spectra of the microbe proteins are recorded using time-of-flight mass spectrometers operating in linear mode, due to the particularly high detection sensitivity, although the mass resolution and mass accuracy of the spectra from time-of-flight mass spectrometers operating in reflector mode is significantly better. In reflector mode, however, only around a twentieth of the ion signals appear and the detection sensitivity is up to two orders of magnitude lower. The reason for the high sensitivity is that, when a time-of-flight mass spectrometer is operating in linear mode, not only the stable ions are detected, but also the fragment ions generated by "metastable" ion decay. Secondary electron multipliers are used to measure the ions, as a result of which even neutral particles created en route as a result of ion decay are measured by the ion detector, since they also generate secondary electrons on impact. All of these fragment ions and neutral particles that have been created from one parent ion species have the same velocity as the parent ion and therefore reach the ion detector at the same time. The time of arrival is a measure of the mass of the original intact ions.

For many applications, the higher detection sensitivity is of such importance that many of the disadvantages of linear operation of the time-of-flight mass spectrometer, such as a significantly lower mass resolution, are accepted. For these applications, the energy of the desorbing and ionizing laser is increased, raising the ion yield but also decreasing their stability, although that is not of great importance here.

Recording mass spectra with time-of-flight mass spectrometers generally requires a large number of single spectra to be recorded and digitized in rapid succession; usually producing a sum spectrum by adding together measurements with the same flight time. The ions for each individual spectrum are generated by a shot from a pulsed UV laser. This method of generating sum spectra is necessary because of the low dynamic range in an individual spectrum. A minimum of 50 and in some cases even 1,000 or more individual spectra are recorded; a sum spectrum generally consists of several hundred individual spectra, and these can be recorded and added together within a few seconds in modern mass spectrometers. The total time required to record a sum spectrum depends on the number of individual spectra and on the firing frequency of the laser being used. Lasers firing at between 20 and 200 hertz are in use nowadays for this purpose, but other electronics as, for instance, delayed acceleration voltages also must be switched correspondingly, determining the applicability of faster lasers. If medium-speed processes are used, somewhere between 2 and 30 seconds are required to record a good sum spectrum.

In the fields of application mentioned above, mass spectra extending from about 1,000 daltons up to the high mass ranges of, for instance, 20,000 daltons are measured. It has been found that the mass signals in the lower range of masses up to about 2,500 daltons cannot be effectively evaluated, as they originate from externally attached non-specific peptides and other substances whose presence tends to be random and variable. For microbes smeared onto the sample support plate, the best identification results are obtained when only the mass signals in the range between about 3,000 and 15,000 daltons are evaluated. For microbes decomposed after thorough cleaning in centrifugation tubes and transfer of the decomposition liquid to a sample plate with pre-prepared thin layer matrix, the mass range from 1000 to 15000 daltons may used since the resulting spectra are much clearer and better reproducible in the lower mass range.

For the reasons of low mass resolution mentioned above, isotope groups cannot be resolved in these mass ranges. The isotope groups consist of ion signals that differ by only one dalton. Only the envelopes of the isotope groups are measured. However, mass spectrometric measurement methods that offer a higher resolution and higher mass accuracy are also known; but it is not yet known whether comparable sensitivities can be achieved with them.

This method for identifying microbes generally requires a pure culture of microbes in order to obtain a mass spectrum that is not overlaid by the signals of other microbes. It has, however, been found that mass spectra from mixtures of two microbe species can be evaluated, and that both species of microbe can be identified. The reliability of the identification is only slightly affected. If more than two microbe species are included in the mass spectrum, the probability and reliability of identification decrease very sharply.

The method for simply identifying microbes by mass spectrometry can find applications in many fields, such as the monitoring of drinking water or quality control in food manufacture. In food manufacture, the species of microorganisms present are crucial to whether the food can be consumed without risk. We need only think of harmful staphylococci, streptococci or salmonella, which must be detected through ongoing checks. On the other hand, beer, wine, cheese and yoghurt could not be created without the useful work of billions of microbes. Purity of the strains is crucial for their use.

Particularly strict and reliable monitoring is required in the medical field. Pathogens must be kept away from hospitals. Constant monitoring of the microbes, and their identification, is a strict statutory requirement for operating rooms, for example.

The identification of microbes involved in infectious illnesses plays a particular role. Here it is important to be able to identify the pathogens very quickly so that the correct medical intervention can be taken immediately. In spite of the need to first grow microbe cultures, the method of mass spectrometric identification is one or two days faster than the microbiological methods used up to now. Nevertheless, it still takes about 12 to 24 hours, and the time can be significantly longer if a second culturing happens to be necessary. For many applications, particularly in the case of acute infections, this time is too long, and the search for faster procedures is urgent.

In WO 2002/021,108 A2 (N. G. Anderson and N. L. Anderson), a method is presented to extract, separate, and purify microbes including viruses by twodimensional ultra-centrifuging directly from body fluids or homogenized tissue. In a first centrifuging step, all particles are removed having a sedimentation speed higher than those of the microbes to be identified. In the second ultra-centrifuging step, isopycnic banding is used in liquids filled in to form a wide-range density gradient, using special serrated centrifuge tubes. The microbanded microbes can be recognized and taken out by complex apparatuses, washed, even centrifuged after washing once more to form pellets, in order to prepare samples containing one kind of microbes only for different types of analysis procedures. "Once the viruses from a biological sample have been highly purified and concentrated by the twodimensional centrifugation technique as described above by using microbanding centrifuge tubes, the viruses are amenable for use in many other assays." (Page 17, line 7). Among the many different types of assays enumerated in the patent, also mass spectrometric analysis with ionization by matrix-assisted laser desorption is mentioned, describing shortly the smearing process onto sample plates with adding matrix solution, according to a cited literature publication. This patent publication is an outstanding description of the various centrifuging procedures which can be applied to body fluids to receive separated species of microbes in complex mixtures of microbes. Interestingly, the claims are directed only to methods and apparatuses to detect and localize light emitted or scattered by the microbanded samples in a centrifuge tube in order to detect the microbands which are difficult to observe.

The objective of the invention is to provide a method with which infectious pathogens in body fluids can be identified preferably within only about one hour.

SUMMARY OF THE INVENTION

The invention is based on the surprising fact that, in the vast majority of cases (well over 70 percent), acute infections in body fluids are attributable to only a single pathogen species that has overgrown all other species of microbe and that these pathogens are always present in very high concentrations of typically between $10^4$ and $10^8$ pathogens per milliliter. In a small proportion of around 15%, two species of pathogens are present in such amounts that both can be detected in the mass spectra. This exclusivity in the types of pathogens present in acute infections is in sharp contrast to the presence of microbes in or on the human body under other circumstances. For instance, the $10^{14}$ bacteria typically found in the human intestines are distributed across at least 400 bacterial species that live in equilibrium with one another.

The invention consists in directly precipitating the pathogens involved in an acute infection from the body fluid, for instance by centrifuging for between 5 and 10 minutes at a speed of at least 10,000 rpm, and, possibly after an optional washing stage followed by further centrifuging, subjecting the pathogens of the pellet to analysis by mass spectrometry. A preferred method consists of decomposing the pathogens in the precipitated pellet by acids and organic solvents, centrifuging once more, and subjecting the supernatant decomposition fluid containing the proteins to mass spectrometric analysis. For reasons presented above, mass spectrometric analysis leads to mass spectra from a single pathogen species in most cases, and in much less cases to mass spectra from mixtures of two pathogen species. Only in a few cases is it not possible to evaluate the mass spectra due to the presence of more than two species of pathogens. The mass spectra can therefore regularly be evaluated successfully; the procedure is extremely fast. If a mass spectrometer is available immediately, and if the working time is optimized, it can be carried out in around 20 to 30 minutes.

The direct precipitation into pellets must sometimes be made possible by adding some low-density fluids like water, methanol or others in order to lower the density of the body fluid to a value below the density of the pathogens. The added liquids, however, must keep the pathogens intact, so that intact pathogens are precipitated: In contrast to WO 2002/021,108 A2, the formation of isopycnic microbands is avoided because the microbands require complex apparatuses for their recognition and their taking out of the liquid, even if that means that some mixtures of pathogens with other pathogens or other body fluid particles are precipitated.

This method can be applied directly and successfully to all clear body fluids such as urine, lacrimal fluid, nasal discharge, lymph, synovial fluid or cerebrospinal fluid. In body fluids which contain corpuscles, such as whole blood or the discharge from an abscess, an intermediate stage for destruction of the corpuscles can be included.

In acute infections, pathogens are usually present in large numbers. For instance, in the case of inflammation of the urinary tract or kidneys, around $10^5$ to $10^7$ pathogens are present in a milliliter of urine. Since only around $10^3$ to $10^4$ microbes are required for mass spectrometric analysis, centrifuging will immediately yield sufficient quantities of pathogens for mass spectrometric identification.

If more than $10^5$ microbial pathogens are present in the centrifuged sample, the deposited pellets are visible to the naked eye. But even if there are fewer microbial pathogens in the body fluid, fast extraction and decomposition methods can be applied successfully to the then invisible pellets. The extraction processes for the proteins in the pathogens are very fast and add only a few minutes to the total analysis time.

It is also possible, if appropriate measures and additives are used, to culture the pathogens in the body fluid directly, as, for instance, with the known method of "blood culture" by directly incubating the bag of whole blood. Such culturing is significantly faster than growing cultures in Petri dishes and can, particularly in the case of heavy infections, often provide sufficient pathogens for identification within an hour.

Acute infections can also be caused by non-microbial pathogens like viruses, Chlamydia and Rickettsia, none of which can be cultured in a nutrient medium, as they can only multiply in host cells. In acute infections, certain forms of these pathogens are found in extremely high numbers in body fluids and can be effectively precipitated in an ultracentrifuge in spite of their small size; it is known that they can also be identified by their specific proteins measured by mass spectrometry. Viruses are present in body fluids in the form of virions. These have highly characteristic coat proteins in the form of a capsid, within which the RNA or DNA of the virus is protected. The coat proteins can be identified by mass spectrometry due to their specificity. Sometimes, lipoproteins of a lipoprotein envelope are found in addition. Chlamydia are found in body fluid in an extracellular form as "elementary bodies"; they, and similar forms of Rickettsia, each carry their own proteins.

Viruses can also be identified through a mass spectrometric analysis of their RNA or DNA, if this is decomposed by special methods of enzymatic digestion.

DESCRIPTION OF THE PREFERRED EMBODIMENTS

The invention provides a basic method for the identification of microbial and non-microbial infectious pathogens in body fluids that is significantly easier and faster than previous methods, most of which involve culturing colonies of the microbes in nutrient media in Petri dishes. The method according to the invention can even be applied to viruses, Chlamydia and Rickettsia, for which the cultivation of colonies in nutrient media is not possible as they only multiply within host cells. The basic method according to the invention consists of separating the pathogens (including viruses) from a body fluid in which infection is suspected by centrifuging the pathogens into pellets, and subjecting the pathogens to mass spectrometric analysis of their proteins for an identification, e.g. by applying matrix-assisted laser desorption to the pathogens smeared onto sample support plates.

If the pathogens are of low density, direct precipitation in a centrifuge might not be possible. The direct precipitation into pellets, therefore, must sometimes be made possible by adding some low-density fluids like water, methanol or others in order to lower the density of the body fluid to a value below the density of the pathogens. The added liquids, however, must keep the pathogens intact, so that intact pathogens are precipitated.

The invention is based on the direct precipitation of the pathogens into pellets, quite in contrast to WO 2002/021,108 A2, which teaches the formation of isopycnic microbands by ultracentrifugation. Microbands are avoided here because they require complex apparatuses for their recognition and their taking out of the liquid.

A preferred derivative of the basic method includes extracting the proteins from the pelleted pathogens still inside the centrifuging tube, centrifuging once more to precipitate the pathogen walls and other non-dissolving particles, and subjecting the dissolved proteins in the supernatant fluid to the mass spectrometric identification process of the pathogens. The mass spectrometric analysis of the supernatant fluid may be based on an ionization of the proteins by electrospray, or by matrix-assisted laser desorption.

A further derivative of the basic method according to the invention consists of culturing the pathogens in the body fluid by incubating, possibly after adding some nutrients, before the pathogens are centrifuged into pellets and subjected to mass spectrometric identification.

The pathogens are most easily separated by brief centrifuging for between 5 and 10 minutes. Viruses require the stronger force of an ultracentrifuge. The resulting pathogen pellet can then be washed one or two times, preferably with distilled water, to remove a high proportion of any associated proteins and other impurities from the body fluid. The centrifuging process is repeated after each washing stage. If the pellet is visible to the naked eye, it can be assumed that it contains at least around 100,000 microbial pathogens.

In this case of a visible pellet, simply smearing the sample on the sample support will in most cases be enough to lead to successful identification. The separated pathogens from the pellet can be applied to a mass spectrometric sample carrier using a small spatula or a small rod, sprinkled with matrix solution and then put into the mass spectrometer after drying and crystallization of the matrix substance. In general, the matrix solution penetrates into the pathogens, causing them to burst due to osmotic effects. Small crystals of matrix substance form as the sample dries and the pathogenic proteins are embedded during the process of crystallization.

This procedure, however, is not always recommendable for several reasons. Extraction and decomposition is, for instance, required if the pathogens in the pellet cannot simply be smeared onto the sample support plate, for instance because the pathogens create a slimy pulp that will not adhere. Another reason is that some species of pathogens have cell walls so strong that they are not destroyed by osmosis when exposed to the organic solvent in the matrix solution on the sample plate. In all these cases, decomposition of the pathogens with extraction of the proteins will always be necessary, but this also takes only a few minutes. If the pellet is not visible, decomposition is always to be recommended.

The most essential reason for applying the decomposition process, however, is the risk of infection of the laboratory personnel. Particular care must be taken with infectious material, as the laboratory physician will know. Due to the risk of infection, it is therefore appropriate to kill off the microbes in some suitable way without changing the proteins at the same time to the extent that identification by means of the protein profile is no longer possible. Here again, the extraction method described below in more detail offers a method of implementing such a hygiene precaution.

The pellets with the separated pathogens are subjected within the centrifuge tube to an extraction process for the proteins prior to the mass spectrometric analysis, by adding suitable acids and suitable organic solvents. The acids weaken the cell walls, and the organic solvents penetrate into the pathogens by osmosis, making them burst and helping to dissolve the internal proteins. The extraction process is also known as the decomposition process.

To go into more detail, the decomposition can, for instance, be achieved through the following protocol: while still in the centrifuging container (for instance an Eppendorf cup) the pellet is dissolved by carefully stirring it with a few microliters of 70-percent formic acid, which greatly weakens the often very tough cell walls, if it does not actually destroy them. After about one minute, an approximately equal quantity of acetonitrile is added, by which the cell walls are finally destroyed by osmotic forces and the proteins released from inside the microbe. The solution is centrifuged once again in order to separate out the solid components such as cell wall fragments. The supernatant, which now contains the pathogenic proteins, is subjected to mass spectrometric analysis by applying drops to the mass spectrometric sample support using a pipette.

There are prefabricated sample support plates with spots of thin layers of matrix substance, onto which the extraction liquid can be pipetted; the matrix substances will be partially dissolved by the added acetonitrile. As a result, the proteins are embedded in the small crystals during recrystallization as the solution dries. Other types of sample plates possess hydrophilic spots within hydrophobic ambience; the extraction liquid can be pipetted onto the hydrophilic spots, mixed with a solution of matrix material, after which it is dried for a few minutes in air, e.g., a warm air stream, or in a vacuum container. Or the matrix solution can already be added to the extraction liquid.

In addition to this method of decomposition using chemical and physico-chemical agents such as acids or organic solvents for osmosis, decomposition can also be done or supported using quite different methods, such as destroying the cell walls by physical means. The cell walls can, for instance, be destroyed by acoustic irradiation, such as in an ultrasonic bath. Mechanical methods can also be used, such as a micro-pestle for crushing or grinding the microbes directly in the centrifuging container.

The method of decomposition supplies very pure, clear mass spectra in a mass range up from about 1000 daltons without any interfering background, and requires only a few additional minutes. It can therefore easily be applied as a standard method in order to avoid altogether the sometimes troublesome and potentially dangerous "smearing" of the intact, still living and highly infectious microbes. If a mass spectrometer is available immediately, identification can be achieved within less than half an hour.

The mass spectrum largely represents the profile of the soluble proteins in the pathogens; the insoluble cell-wall proteins of the microbes are generally not visible in the mass spectrum. As is known to the specialist in the field, for proteins of low solubility, such as the coat proteins of viruses, the solubility can be increased through the use of special solvents. It is quite possible for some substances that are not proteins to appear in the mass spectrum; for simplicity, however, the term "protein profiles" will be used here to refer to the mass spectra of the pathogens.

For mass spectrometric analysis with ionization by matrix-assisted laser desorption, the sample support plate with the dry samples is inserted through a vacuum lock into the vacuum system of a mass spectrometer. The matrix crystals with the embedded protein molecules are then exposed to pulsed laser light in the ion source of the mass spectrometer; this creates ionized protein molecules in a plasma vapor cloud; the ion masses of the different types of protein ions can then be measured in the mass spectrometer. Preferably, a time-of-flight mass spectrometer with a linear flight path, not employing a reflector, is used for this purpose. The time-of-flight mass spectrometer separates the electrically accelerated ions because, given the same energy by the same accelerating force in the electrical field, the heavier ions have a lower flight velocity than the lighter ions. The time-resolved ion current at a detector located at the end of the flight path therefore directly constitutes a mass spectrum from light to heavy ions, because the relationship between flight times and masses is known. The mass spectrum is the intensity profile of the mass values of the proteins, each with genetically determined characteristic masses.

The supernatant fluid may also be analysed by electrospray ionization, e.g., in a time-of-flight mass spectrometer with orthogonal ion acceleration (EI-OTOF-MS). The mass spectra obtained are highly mass resolved, but look very different because electrospray ionization delivers multiply protonated ions, particularly for ions in the interesting mass range from m=1,000 to 20,000 daltons. There are methods, however, to compute a virtual mass spectrum of the protein ions, as it looks with ions of single charges only. The computer programs use the fact that the high mass resolution exhibit the isotopic pattern and thereby the number of charges for each species of protein ion. On the other hand, there are methods to deprotonate the ions down to singly-charged ions by adding deprotonating anions to the multiply charged protein ions in special reaction cells.

The mass spectrum of the pathogen's proteins must then be compared with reference spectra from a library, and the pathogens are thereby identified on the basis of similarity criteria between the mass spectra. This method is part of the prior art, and is known to those skilled in the art. Reliable libraries of the mass spectra of the protein profiles of microbes, suitable for medical and legal applications (said to be "validated"), are being developed at many sites, including a variety of central national institutes, e.g. for the monitoring and prevention of disease. Libraries containing validated reference spectra for around 1,500 microbe species and about 3,000 strains are known; these libraries are being extended every day.

The invention is thus based on what, in essence, is a known method of mass spectrometric identification of microbes, but without the otherwise invariably used, time-consuming preparation of microbe cultures in an external nutrient medium. The invention obtains the pathogens directly from the body fluid, in which they are present, in cases of acute infections, with sufficient purity of species, in contrast to the microbes found elsewhere in or on the human body.

The method is thus surprisingly simple; it is substantially based on the observation that in the great majority of acute infections, only one, or at most two, species of pathogens is found in the body fluid above the threshold of detection. And their concentration is surprisingly high. As a result, when these pathogens are sedimented from the body fluid in a centrifuge, the quantities of pathogens obtained provide enough sample substance for measurement, on the one hand, and represent sufficiently pure pathogen cultures, on the other hand. Even in the presence of two pathogen species, the method still operates satisfactorily.

The separation of pure pathogen species, which otherwise is achieved through time-consuming culturing of separated colonies in nutrient media, is thus avoided with this method.

In some cases, the method according to the invention even offers advantages over the purification of pathogen species by culturing because there are pathogens that cannot be cultured in the usual, external nutrient media, such as the frequently occurring and highly infectious Chlamydia and Rickettsia, both of which can only thrive inside other cells. Chlamydia and Rickettsia are microbe species that can only multiply within host cells, but, in contrast to viruses, they develop their own metabolism. Chlamydia only multiply in their form as "reticular bodies" within host cells; outside host cells they are only found as "elementary bodies", with practically no metabolism. They can be detected in the first flow of urine or in the discharge from the genital area if they are present as a genital infection (by far the most common sexually transmitted disease in Europe). Chlamydia also cause eye diseases (with loss of sight; common in Africa) and pulmonary diseases; they can be found in the synovial fluid of the knee joint and in many other organs as dangerous pathogens, but are not easy to detect. At present, successful identification is usually only possible by DNA sequencing after PCR multiplication; in other words, a time-consuming method.

In the same way, viruses in the form of virions can be obtained from body fluids by ultracentrifuging in sufficiently large quantities to permit mass spectrometric identification. The mass spectrum here primarily displays the coat proteins of the capsid and, sometimes, the additional lipoprotein envelope. The coat proteins are manufactured in the host cell specifically by the genetic program of the virus, and are therefore highly characteristic of the individual virus species. Thirty or more different proteins, which combine to form a regularly shaped coat of the virus, may be involved. The coat proteins require a special decomposition process in order to dissolve them for incorporation into the matrix crystals. The lipoprotein envelope, which is present in some kinds of virions, is formed when the virions which have been grown in the cell are ejected into the surroundings through particular excrescences in the cell membrane; the virions then take the lipoproteins with them.

The applicability of the method to viruses, Rickettsia and Chlamydia gives the invention a special and outstanding significance, as the microbiological identification of these pathogens is a long and difficult process. They cannot be cultivated in standard nutrient media, but require host cells in order to multiply. Reliable microbiological identification is carried out by DNA sequencing, often requiring a week or more, whereas mass spectrometric identification takes only a few hours or less.

Although science does not at present consider viruses to be living organisms, they are, as usual, included in this document under the term "pathogens". Rickettsia and, in particular, Chlamydia, which even until the 1970s were classified as viruses, are now officially considered to be microbes.

The body fluids of interest are primarily the clear fluids. These include fluids excreted by the body, such as urine, lacrimal fluid, sputum and nasal secretion, but also internal body fluids, such as lymph, synovial fluid (obtained by arthrocentesis) or cerebrospinal fluid (obtained by lumbar puncture). In the presence of acute infections, these fluids contain large quantities of pathogens, in the range of between $10^4$ and $10^8$ pathogens per milliliter. If these fluids, nasal secretion for instance, contain mucous substances (usually protein solutions), they can be diluted with suitable liquids in order to facilitate separation of the microbes.

The pathogens responsible for inflammation of the urinary tract can, for instance, be detected in urine. The 20 to 30 different types of pathogen responsible for meningitis can be found in the cerebrospinal fluid.

Body fluids containing a large number of particles, such as whole blood, pus or cloudy discharges, can also be identified by the method according to the invention, but do require additional steps in order to destroy and remove the particles.

The method can be applied to infected whole blood as follows: if the whole blood already contains enough pathogens, as in the case of acute sepsis, the pathogens can be directly separated together with the blood particles by centrifuging. If the pellet is then dissolved in distilled water, the blood particles, which only have weak cell membranes, are destroyed by osmosis, but the microbes are not. Washing and further centrifuging then deposits a pellet containing well enriched microbes. Decomposition and mass spectrometric analysis here often lead directly to very rapid success, as is necessary in the case of acute sepsis.

If the quantity of pathogens in the blood is not sufficient for this direct method, then the pathogens can be cultured in the whole blood inside the blood bag. Some nutrient medium may be added to the blood for this purpose, and the blood bag is placed in an incubator at a favorable temperature. This method can increase the number of pathogens by a factor of about ten within an hour in favorable cases; usually, however, several hours are required in order to culture sufficient quantities of the infection-causing pathogen. But this is still a great deal quicker than culturing in an external nutrient medium. It may be necessary to add suitable substances, such as ion-exchange resins, to the blood in order to bind any antibiotics that may have been administered to the patient. The success of culturing pathogens in whole blood can be detected by the formation of gas (carbon dioxide) generated by the growing pathogens.

It is to be expected that, with suitable preparation, the pathogens present in the secretion from abscesses (pus) can be measured directly, although it is possible that no single pathogen species will predominate sufficiently to permit identification without further purification.

If it is expected that the pathogens which require identification are to be, found inside human cells contained in the body fluid, then the procedure described for whole blood can be applied to homogenized tissue. After centrifuging, the human cells can be destroyed by distilled water, as osmosis causes their membranes to burst.

The methods described here can be modified in many ways by those skilled in the art with knowledge of the invention. Some of these modifications have already been indicated above; but there are certainly other methods which, on the basis of the fundamental principle of direct separation, can generate the highly informative mass spectra that are required for identification of the pathogens.

I claim:

1. A method for the mass spectrometric identification of pathogens in a blood sample, the method comprising the steps of:
    (a) destroying blood particles in the blood sample;
    (b) precipitating by centrifuging the pathogens without further multiplication from the blood sample directly into a pellet;
    (c) subjecting the pathogens to a mass spectrometric analysis of their proteins; and
    (d) identifying the pathogens by comparison of protein mass spectra with reference protein mass spectra.

2. The method according to claim 1, wherein in step (c) the pathogens in the pellet are smeared directly onto mass spectrometric sample support plates and sprinkled with matrix solution for ionization of their proteins by matrix-assisted laser desorption.

3. The method according to claim 1, wherein in step (c) the proteins are extracted from the pathogens using an extraction fluid while the pellet with the pathogens rests in a centrifuge tube, and the fluid is subjected to mass spectrometric measurement.

4. The method according to claim 3, wherein the extraction fluid is subjected to mass spectrometric analysis using electrospray ionization.

5. The method according to claim 3, wherein the extraction fluid is subjected to mass spectrometric analysis using ionization by matrix-assisted laser desorption.

6. The method according to claim 5, wherein the extraction fluid is applied to a mass spectrometric sample support plate onto which a layer of matrix crystals has already been deposited.

7. The method according to claim 5, wherein a matrix substance solution is added to the extraction fluid before this is applied to the sample support plate.

8. The method according to claim 1, wherein, for extraction of the proteins, the pathogens of the pellets are decomposed by chemical, physico-chemical or physical means.

9. The method according to claim 8, wherein the extraction fluid is subjected to mass spectrometric analysis using electrospray ionization.

10. The method according to claim 8, wherein the extraction fluid is subjected to mass spectrometric analysis using ionization by matrix-assisted laser desorption.

11. A method for the mass spectrometric identification of pathogens in a blood sample, the method comprising the steps of:
- (a) precipitating by centrifuging the pathogens without further multiplication from the blood sample together with blood particles into a pellet;
- (b) destroying the blood particles in the pellet;
- (c) subjecting the pathogens to a mass spectrometric analysis of their proteins; and
- (d) identifying the pathogens by comparison of protein mass spectra with reference protein mass spectra.

12. The method according to claim 11, wherein the blood particles which are present in the pellet are destroyed by osmosis.

13. The method according to claim 12, wherein distilled water is used for destroying the blood particles in the pellet by osmosis.

14. The method according to claim 11, wherein a further centrifuging after step (b) deposits a pellet containing enriched pathogens.

* * * * *